US012677809B2

(12) United States Patent
Arimoto et al.

(10) Patent No.: US 12,677,809 B2
(45) Date of Patent: Jul. 14, 2026

(54) CEPHALOPOD REARING METHOD, CEPHALOPOD REARING APPARATUS, PROTOZOA PREVENTION METHOD, AND PROTOZOA EXTERMINATION METHOD

(71) Applicant: Nissui Corporation, Tokyo (JP)

(72) Inventors: Ippei Arimoto, Saiki (JP); Kentaro Fujii, Saiki (JP); Kagayaki Morishima, Saiki (JP)

(73) Assignee: NISSUI CORPORATION, Tokyo (JP)

( * ) Notice: Subject to any disclaimer, the term of this patent is extended or adjusted under 35 U.S.C. 154(b) by 23 days.

(21) Appl. No.: 18/670,543

(22) Filed: May 21, 2024

(65) Prior Publication Data

US 2024/0306619 A1     Sep. 19, 2024

Related U.S. Application Data

(63) Continuation-in-part of application No. PCT/JP2022/042420, filed on Nov. 15, 2022.

(30) Foreign Application Priority Data

Nov. 22, 2021     (JP) ................................. 2021-189453

(51) Int. Cl.
*A01K 63/04*          (2006.01)
*A01K 61/00*          (2017.01)
*A01K 67/30*          (2025.01)
(52) U.S. Cl.
CPC .............. *A01K 63/04* (2013.01); *A01K 61/00* (2013.01); *A01K 67/30* (2025.01)

(58) Field of Classification Search
None
See application file for complete search history.

(56) References Cited

U.S. PATENT DOCUMENTS

| | | | | |
|---|---|---|---|---|
| 3,473,509 A | * | 10/1969 | Miyamura | ............. A01K 61/00 119/212 |
| 6,959,663 B2 | * | 11/2005 | Hjaltason | ............. A23K 20/158 119/230 |
| 12,389,885 B2 | * | 8/2025 | Chen | ...................... A01K 61/00 |
| 2015/0114304 A1 | | 4/2015 | Pierce | |
| 2020/0367476 A1 | | 11/2020 | Tur Estrada et al. | |
| 2024/0306614 A1 | * | 9/2024 | Arimoto | ................ A23K 10/30 |

(Continued)

FOREIGN PATENT DOCUMENTS

| | | |
|---|---|---|
| CN | 101731176 A | 6/2010 |
| CN | 103548721 A | 2/2014 |
| CN | 103583456 A | 2/2014 |

(Continued)

OTHER PUBLICATIONS

CN-109362610-A English Translation (Year: 2019).*

(Continued)

*Primary Examiner* — Magdalena Topolski
(74) *Attorney, Agent, or Firm* — Banner & Witcoff, Ltd.

(57)          ABSTRACT

Provided herein is a method for breeding cephalopod larvae in a rearing tank having a water changing means. The method includes a water-changing period during which the ratio of water changed by the water-changing means per day is 200% or more relative to the quantity of water in the rearing tank in a floating breeding period of the cephalopod larvae.

25 Claims, 1 Drawing Sheet

(56)           References Cited

U.S. PATENT DOCUMENTS

2024/0306618 A1 * 9/2024 Fujii ..................... A01K 67/30

FOREIGN PATENT DOCUMENTS

| | | | | | |
|----|----------------|------|---|---------|-------------|
| CN | 108450393 | A | * | 8/2018 | ............ A01K 63/04 |
| CN | 109362610 | A | * | 2/2019 | ............ A01K 61/00 |
| CN | 113749021 | A | * | 12/2021 | ............ A01K 61/00 |
| CN | 118284334 | A | | 7/2024 | |
| EP | 2815641 | A1 | * | 12/2014 | ............ A01K 63/04 |
| JP | 2007289941 | A | * | 11/2007 | |
| JP | 2017-006054 | A | | 1/2017 | |
| JP | 2020-0074761 | A | | 5/2020 | |
| JP | 2020150821 | A | * | 9/2020 | |
| JP | 2021-136918 | A | | 9/2021 | |
| KR | 20060023078 | A | * | 3/2006 | ............ C02F 3/327 |

OTHER PUBLICATIONS

Arai-Osuke at al., "Effect of Feed Amount of Ikanago Fine Meat on Growth and Fatty Acid Composition of Palma Dako Floating Phase Larvae," *Aquaculture Science*, vol. 56, No. 4, pp. 595-600, 2008.

Dan et al., "An upwelling system for culturing common octopus paralarvae and its combined effect with supplying natural zooplankton on paralarval survival and growth," *Aquaculture*, vol. 495, pp. 98-105, 2018.

O. Masaichi, "Significant advances in production technology for young dako," Fiscal 2018 Presentation Meeting of Research Results at the Fisheries Research Laboratory in the Seto Inland Sea, 2018.

Uriarte et al., "Rearing and Growth of the Octopus *Robsonella fontaniana* (Cephalopoda: Octopodidae) From Planktonic Hatchlings to Benthic Juveniles," *Biological Bulletin*, vol. 218, pp. 200-210, 2010.

Villanueva et al., "Growth and proteolytic activity of *Octopus vulgaris* paralarvae with different food rations during first feeding, using *Artemia nauplii* and compound diets," *Aquaculture*, vol. 205, pp. 269-286, 2002.

International Search Report mailed Feb. 14, 2023 in International Application No. PCT/JP2022/042420.

International Preliminary Report on Patentability mailed Jun. 6, 2024 in International Application No. PCT/JP2022/042420.

Tiago de Moraes Lenz et al, "First attempts of the use of intake tracers in encapsulated diets with chitosan for octopus paralarvae", Aquaculutre Reserch, Blackwell Science, Oxford, GB,vol. 50, No. 10, Jul. 1, 2019, p. 3070-p. 3073.

* cited by examiner

1

CEPHALOPOD REARING METHOD, CEPHALOPOD REARING APPARATUS, PROTOZOA PREVENTION METHOD, AND PROTOZOA EXTERMINATION METHOD

CROSS-REFERENCE TO RELATED APPLICATIONS

This Application is a Continuation-in-part of Application PCT/JP2022/042420 filed on Nov. 15, 2022. Application PCT/JP2022/042420 claims priority from Application 2021-189453 filed on Nov. 22, 2021 in Japan. The entire contents of these applications are incorporated herein by reference in their entirety.

TECHNICAL FIELD

The present disclosure relates to a cephalopod rearing method, a cephalopod rearing apparatus, a protozoa prevention method, and a protozoa extermination method.

BACKGROUND ART

In recent years, since consumers have strong preference and interests in resource conservation, there is a demand for the development of aquaculture techniques for cephalopods.

For example, Patent Document 1 discloses an octopus raising shelter and an octopus aquaculture system.

CITATION LIST

Patent Literature

Patent Document 1: JP 2017-006054 (A)

SUMMARY OF INVENTION

Technical Problem

As a technique for increasing the production of cephalopods, it is required to reduce the mortality rate of larvae. However, known aquaculture techniques have a problem that the mortality rate is often high.

An object of the present disclosure is to provide a technique for reducing the mortality rate in the rearing of cephalopod larvae.

Solution to Problem

The present disclosure provides the following inventions.

[1] A cephalopod rearing method including rearing cephalopod larvae in a rearing tank including a water exchange mechanism, wherein a planktonic paralarval stage for the cephalopod larvae includes a high water exchange rate period in which a water exchange rate relative to an amount of water in the rearing tank per day by the water exchange mechanism is 200% or more.

[2] The cephalopod rearing method according to [1], wherein the high water exchange rate period is set to include a period until the cephalopod larvae reach 15 days after hatching.

[3] The cephalopod rearing method according to [1] or [2], wherein the high water exchange rate period is a continuous period of 12 hours or more.

[4] The cephalopod rearing method according to any one of [1] to [3], wherein the high water exchange rate period is set to a period after the cephalopod larvae reach 5 days after hatching.

2

[5] The cephalopod rearing method according to any one of [1] to [4], further including, before the high water exchange rate period, an adjustment period in which the water exchange rate relative to the amount of water in the rearing tank per day by the water exchange mechanism is 100% or less.

[6] The cephalopod rearing method according to [5], wherein the adjustment period is set to a period until the cephalopod larvae reach 10 days after hatching.

[7] The cephalopod rearing method according to any one of [1] to [6], wherein the water exchange mechanism is configured to discharge water in the vicinity of a bottom of water in the rearing tank.

[8] A cephalopod rearing method including rearing cephalopod larvae in a rearing tank, wherein the method includes, in a planktonic paralarval stage for the cephalopod larvae, controlling a density of protozoa of water in the rearing tank to 400 individuals/ml or less.

[9] The cephalopod rearing method according to [8], wherein the rearing tank includes a water exchange mechanism, and the planktonic paralarval stage includes a high water exchange rate period in which a water exchange rate relative to an amount of water in the rearing tank per day by the water exchange mechanism is 200% or more.

[10] The cephalopod rearing method according to [9], wherein the high water exchange rate period is set to include a period until the cephalopod larvae reach 15 days after hatching.

[11] The cephalopod rearing method according to [9] or [10], wherein the high water exchange rate period is a continuous period of 12 hours or more.

[12] The cephalopod rearing method according to any one of [9] to [11], wherein the high water exchange rate period is set to a period after the cephalopod larvae reach 5 days after hatching.

[13] The cephalopod rearing method according to any one of [9] to [12], further including, before the high water exchange rate period, an adjustment period in which the water exchange rate relative to the amount of water in the rearing tank per day by the water exchange mechanism is 100% or less.

[14] The cephalopod rearing method according to [13], wherein the adjustment period is set to a period until the cephalopod larvae reach 10 days after hatching in the rearing period.

[15] The cephalopod rearing method according to any one of [9] to [14], wherein the water exchange mechanism is configured to discharge water in the vicinity of a bottom section of the water contained in the rearing tank.

[16] The cephalopod rearing method according to any one of [9] to [15], wherein a protozoa to be measured for the density of protozoa is a ciliate.

[17] A cephalopod rearing apparatus comprising: a rearing tank for rearing cephalopod larvae; and a water exchange mechanism configured to exchange water in the rearing tank; wherein the water exchange mechanism is configured to exchange water so that a water exchange rate relative to an amount of water in the rearing tank per day is 200% or more in a high water exchange rate period included in a planktonic paralarval stage for the cephalopod larvae.

[18] The cephalopod rearing apparatus according to [17], wherein the high water exchange rate period is set to include a period until the cephalopod larvae reach 15 days after hatching.

[19] The cephalopod rearing apparatus according to or [18], wherein the high water exchange rate period is a continuous period of 12 hours or more.

[20] The cephalopod rearing apparatus according to any one of to [19], wherein the high water exchange rate period is set to a period after the cephalopod larvae reach 5 days after hatching.

[21] The cephalopod rearing apparatus according to any one of to [20], wherein the water exchange mechanism is configured to exchange water so that the water exchange rate relative to the amount of water in the rearing tank per day is 100% or less in an adjustment period before the high water exchange rate period.

[22] The cephalopod rearing apparatus according to [21], wherein the adjustment period is set to a period until the cephalopod larvae reach 10 days after hatching.

[23] The cephalopod rearing apparatus according to any one of to [22], wherein the water exchange mechanism comprises a water discharge mechanism configured to discharge water in the vicinity of a bottom of water in the rearing tank.

[24] The cephalopod rearing apparatus according to any one of to [23], wherein, in the planktonic paralarval stage, a density of protozoa of water in the rearing tank is controlled to 400 individuals/ml or less.

[25] The cephalopod rearing apparatus according to [24], wherein a protozoan to be measured for the density of protozoa is a ciliate.

[26] A protozoa prevention method including preventing occurrence of protozoa in a rearing tank including a water exchange mechanism when rearing cephalopod larvae in the rearing tank, wherein a planktonic paralarval stage for the cephalopod larvae includes a high water exchange rate period in which a water exchange rate relative to an amount of water in the rearing tank per day by the water exchange mechanism is 200% or more.

[27] The protozoa prevention method according to [26], wherein the high water exchange rate period is set to include a period until the cephalopod larvae reach 15 days after hatching.

[28] The protozoa prevention method according to or [27], wherein the high water exchange rate period is a continuous period of 12 hours or more.

[29] The protozoa prevention method according to any one of to [28], wherein the high water exchange rate period is set to a period after the cephalopod larvae reach 5 days after hatching.

[30] The protozoa prevention method according to any one of to [29], further including, before the high water exchange rate period, an adjustment period in which the water exchange rate relative to the amount of water in the rearing tank per day by the water exchange mechanism is 100% or less.

[31] The protozoa prevention method according to [30], wherein the adjustment period is set to a period until the cephalopod larvae reach 10 days after hatching.

[32] The protozoa prevention method according to any one of to [31], wherein the water exchange mechanism is configured to discharge water in the vicinity of a bottom of water in the rearing tank.

[33] The protozoa prevention method according to any one of to [32], wherein the protozoa is a ciliate.

[34] The protozoa prevention method according to any one of to [33], wherein, in the planktonic paralarval stage, a density of protozoa of water in the rearing tank is controlled to 400 individuals/ml or less.

[35] A protozoa extermination method including exterminating protozoa in a rearing tank including a water exchange mechanism when rearing cephalopod larvae in the rearing tank, wherein a planktonic paralarval stage for the cephalopod larvae includes a high water exchange rate period in which a water exchange rate relative to an amount of water in the rearing tank per day by the water exchange mechanism is 200% or more.

[36] The protozoa extermination method according to [35], wherein the high water exchange rate period is set to include a period until the cephalopod larvae reach 15 days after hatching.

[37] The protozoa extermination method according to or [36], wherein the high water exchange rate period is a continuous period of 12 hours or more.

[38] The protozoa extermination method according to any one of to [37], wherein the high water exchange rate period is set to a period after the cephalopod larvae reach 5 days after hatching.

[39] The protozoa extermination method according to any one of to [38], further including, before the high water exchange rate period, an adjustment period in which the water exchange rate relative to the amount of water in the rearing tank per day by the water exchange mechanism is 100% or less.

[40] The protozoa extermination method according to [39], wherein the adjustment period is set to a period until the cephalopod larvae reach 10 days after hatching.

[41] The protozoa extermination method according to any one of to [40], wherein the water exchange mechanism is configured to discharge water in the vicinity the bottom of the rearing tank.

[42] The protozoa extermination method according to any one of to [41], wherein the protozoa is a ciliate.

[43] The protozoa extermination method according to any one of to [42], wherein, in the planktonic paralarval stage, a density of protozoa of water in the rearing tank is controlled to 400 individuals/ml or less.

Advantageous Effects of Invention

According to the present disclosure, there is provided a technique for reducing the mortality rate in the rearing of cephalopod larvae.

DESCRIPTION OF EMBODIMENTS

Figure 1A:
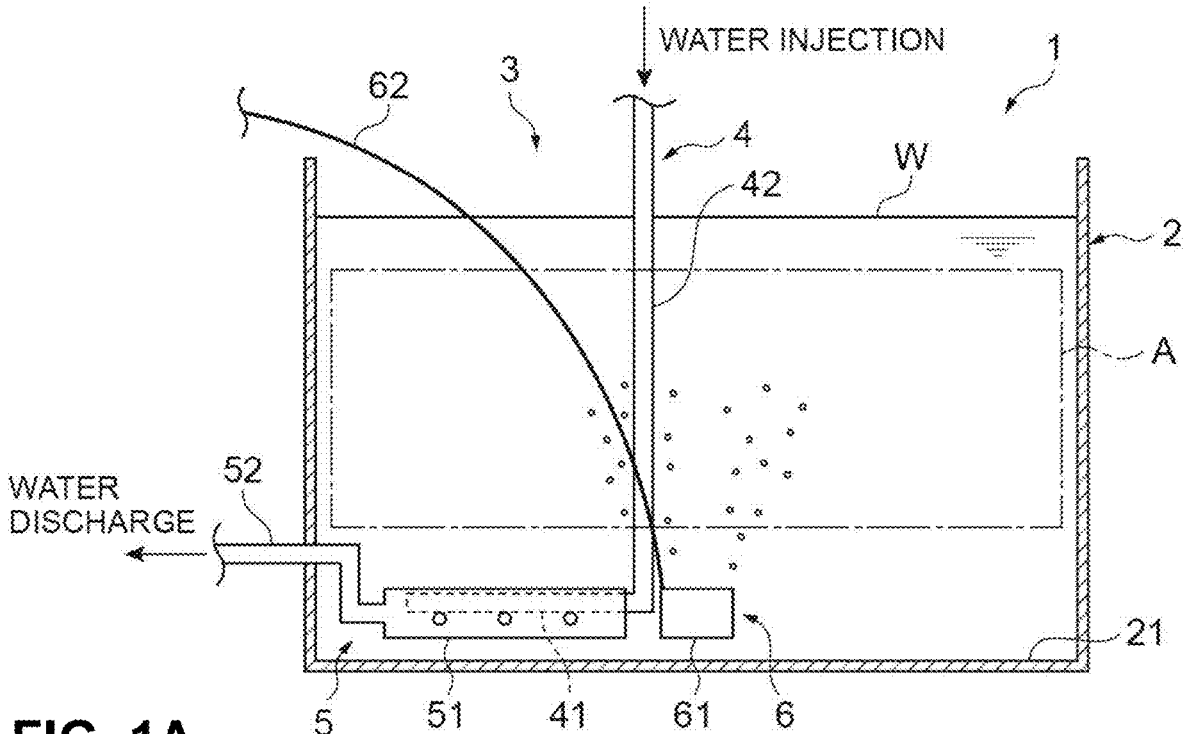
FIGS. 1A and 1B are schematic configuration diagrams of a cephalopod rearing apparatus according to the present embodiment.
Figure 1B:
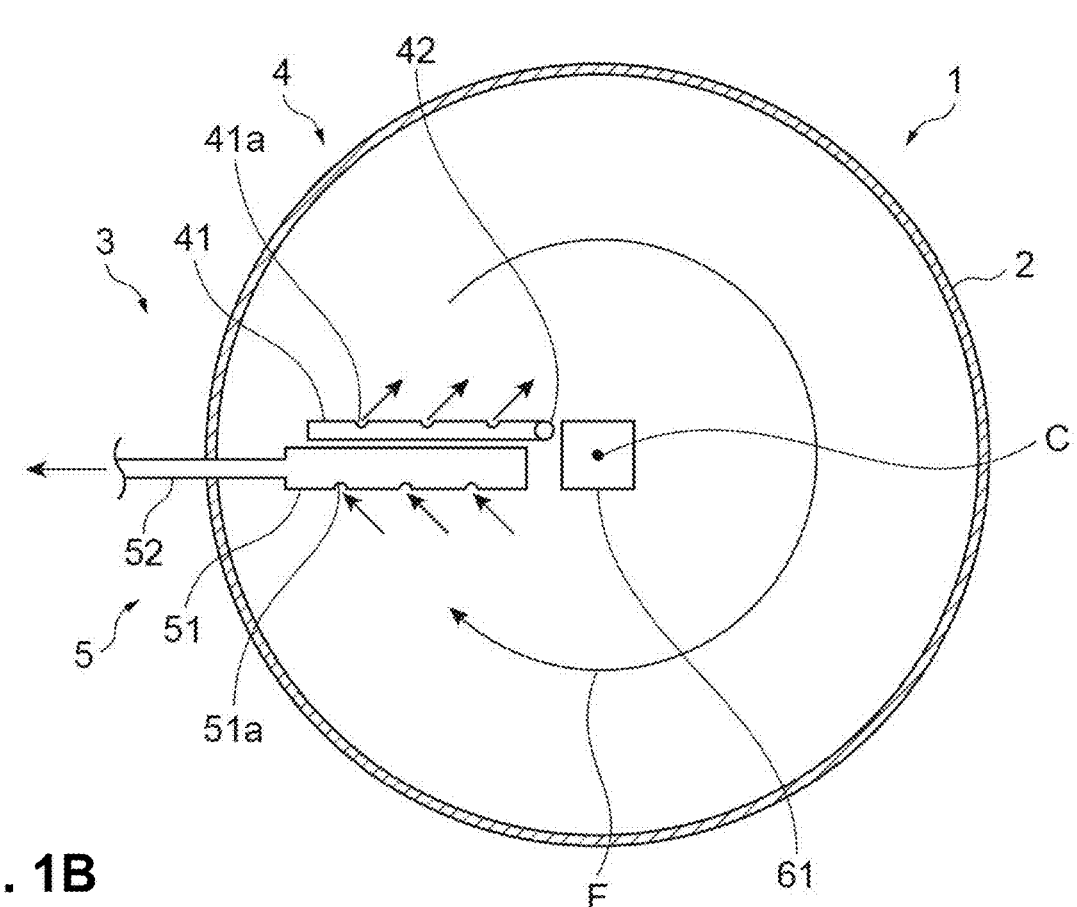

Hereinafter, embodiments for carrying out the present disclosure will be described in detail with reference to the accompanying drawings. In the description of the drawings, the same elements are denoted by the same reference signs, and redundant descriptions of such elements will be omitted.
Cephalopod Rearing Apparatus and Cephalopod Rearing Method FIGS. 1A and 1B include schematic diagrams of the configuration of a cephalopod rearing apparatus described in the present embodiment. As illustrated in FIGS. 1A and 1B, a cephalopod rearing apparatus 1 includes: a rearing tank 2 for rearing cephalopods; and a water exchange unit 3 serving as a water exchange mechanism in the rearing tank 2. FIG. 1A illustrates a vertical cross section of the rearing tank 2, and FIG. 1B illustrates a top view of a vicinity of a bottom surface of the rearing tank 2. In the rearing tank 2, cephalopods are reared by using salt water for rearing. In the present specification, salt water may be simply referred to as water.

The cephalopods to be reared by using the cephalopod rearing apparatus 1 are not particularly limited, and are types of which hatched larvae in a growth stage float in the sea. Examples of such cephalopods include, but are not limited to, oval squid, Japanese common squid, spear squid, *Octopus maya, Octopus ocellatus*, common octopus, North Pacific giant octopus, *Octopus conispadiceus*, and *Octopus minor.*

As described above, the cephalopod floats in water in the rearing tank 2 in a larval stage after hatching. The cephalopod rearing apparatus 1 described above can be used in a planktonic paralarval stage of cephalopod larvae. As used herein, the term "planktonic paralarval stage" refers to a period of rearing in a floating state after hatching and before the benthic phase. For example, in the case of the common octopus, the planktonic paralarval stage is approximately from 0 to 23 days after hatching. In the present disclosure, the term "days after hatching" refers to the number of days elapsed since hatching, expressed in days, and the day of hatching is 0 days after hatching. In addition, in the case of the common octopus, typically, the body length of the common octopus in a rearing floating stage is approximately 0.8 mm or less. The days after hatching and body length of the common octopus in the planktonic paralarval stage may vary depending on the rearing environment, and the days after hatching and body length in a benthic transition period vary depending on the species. Therefore, a usable duration of the cephalopod rearing apparatus 1 may be set individually depending on the species.

As illustrated in FIGS. 1A and 1B, the cephalopod rearing apparatus 1 includes a water exchange unit 3 configured to exchange water in the rearing tank 2. If the water in the rearing tank 2 is not exchanged, leftover feeds of the cephalopod larvae, excreta of the cephalopod larvae, or dead individuals may be rotten, or an ammonia concentration may increase, which may affect the growth of the cephalopod larvae. Therefore, it is necessary to exchange water during the rearing of cephalopod larvae. The water exchange unit 3 includes a water injection unit 4 and a water discharge unit 5. As illustrated in FIGS. 1A and 1B, the water exchange unit 3 may include aeration equipment 6. In addition to the equipment illustrated in FIGS. 1A and 1B, the cephalopod rearing apparatus 1 may be provided with equipment associated with cephalopod rearing, such as feed supply equipment.

The shape, volume, and the like of the rearing tank 2 are not particularly limited. FIGS. 1A and 1B illustrate an example in which the shape of a space for storing water W, which is salt water for rearing, inside the rearing tank 2, is a cylindrical shape having a circular bottom surface. In a case where water is stored in a space that is circular in plan view and cylindrical as illustrated in FIGS. 1A and 1B, it is possible to suppress the deviation of movement of water in the rearing tank 2 to some extent. As for the volume, it is preferable to secure a volume sufficient for rearing the cephalopod larvae in the planktonic paralarval stage. The volume of the rearing tank 2 may be, for example, from 100 L to $150\times10^3$ L, or may be from 500 L to $150\times10^3$ L. The cephalopod larvae may be charged into the rearing tank 2 so that the number of cephalopod larvae per L of the water W is from 1 to 10.

The water injection unit 4 is configured to supply salt water for rearing into the rearing tank 2. The saltwater for rearing may be, for example, seawater subjected to a predetermined treatment such as a sterilization treatment. The water injection unit 4 is not particularly limited as long as it has a configuration in which water is supplied to the rearing tank 2. For example, the water injection unit 4 may include a water injection pipe 41 serving as the water injection mechanism and a pipe 42 extending to the water injection pipe 41.

The water injection pipe 41 is, for example, a long cylindrical pipe arranged in the vicinity of a bottom wall 21, which is a bottom of water, and extending in parallel to the bottom of the water. For example, a plurality of openings 41a are provided in a side surface of the water injection pipe 41 along its extending direction. The pipe 42 is a pipe configured to supply water to be injected into the rearing tank 2 from an external supply source to the water injection pipe 41. Examples of the external supply source include a water tank or tank for storing saltwater subjected to the predetermined treatment. Although not illustrated, water injection through the water injection pipe 41 may be performed by driving a pump provided in the pipe 42, for example.

The vicinity of the bottom of the water in the rearing tank 2 refers to a height range of 10% or less relative to a depth of the water W in the rearing tank 2 or 15 cm or less from the bottom of the water. The bottom of the water corresponds to the bottom wall 21 of the rearing tank 2. In the rearing tank 2, the cephalopod larvae do not float in the vicinity of the bottom of the water, but float in a floating region A near a height range of 20% to 85% from the bottom of the water relative to the depth of the water W, for example. Therefore, the height position at which the water injection pipe 41 is arranged is lower than the floating region A and is closer to the bottom of the water.

For example, as illustrated in FIG. 1B, the water injection pipe 41 may be arranged to extend in a radial direction from a center C of the rearing tank 2. In addition, the water injection pipe 41 may be arranged, for example, at substantially the same position as a water discharge pipe 51 which will be described later. As illustrated in FIG. 1B, when the water injection pipe 41 is provided in the vicinity of the bottom of the water in the rearing tank 2, the water injected through the openings 41a forms a water flow near the bottom of the water, and thus the movement of a sediment in the vicinity of the bottom of water can be promoted. Note that the location where the water injection pipe 41 is installed is not limited to the vicinity of the bottom of the water.

As illustrated in FIG. 1B, the openings 41a of the water injection pipe 41 may be provided not in a direction facing the water discharge pipe 51 but in a side surface on a side away from the water discharge pipe 51. In this case, the water supplied through the openings 41a into the rearing tank 2 is prevented from being directly introduced into the water discharge pipe 51.

The water discharge unit 5 is configured to discharge the water in the rearing tank 2. The water discharge unit 5 is not particularly limited as long as it can discharge the water in the rearing tank 2 out of the rearing tank. For example, the water discharge unit 5 may include a water discharge pipe 51 configured to take in the water in the rearing tank 2 and a pipe 52 configured to discharge the water from the water discharge pipe 51 to the outside of the rearing tank 2.

The water discharge pipe 51 is, for example, a long cylindrical pipe arranged in the vicinity of a bottom wall 21, which is the bottom of water, and extending in parallel to the bottom of water, similar to the water injection pipe 41. For example, a plurality of openings 51a is provided in a side surface of the water discharge pipe 51 along its extending direction. Unlike the example illustrated in FIGS. 1A and 1B, an apparatus may be considered in which the water injection pipe 41 of the water injection unit 4 is provided in the vicinity of the water surface of the rearing tank 2 and the water discharge pipe 51 of the water discharge unit 5 is provided to extend in the vertical direction at the center of the rearing tank 2. In a case where cephalopod larvae are reared in this apparatus, protozoa are observed at an earlier age after hatching, and a survival rate is reduced, as compared with in the rearing of cephalopod larvae in an apparatus in which the water discharge pipe 51 is arranged in the vicinity of the bottom of the water. Therefore, the water discharge pipe 51 is preferably arranged in the vicinity of the bottom of the water. A filter, a net, or the like, may be attached to the openings 51a so that the cephalopod larvae being reared are not discharged from the rearing tank 2 simultaneously with water discharge. The pipe 52 is configured to connect the water discharge pipe 51 to the outside, and convey and discharge the water in the water tank, which has been introduced into the water discharge pipe 51, to the outside. The internal water may be discharged to, for example, the ocean. Before the water is discharged to the ocean or the like, sterilization treatment may be performed on the water to be discharged. The sterilization treatment may be a treatment using a drug, chlorine, ozone, electricity, a filter, or the like, or a combination thereof, as long as live bacteria or protozoa are not discharged as they are. Although not illustrated, water discharge through the water discharge pipe 51 may be performed by driving a pump provided in the pipe 52, for example.

For example, as illustrated in FIG. 1B, the water discharge pipe 51 may be arranged to extend in the radial direction from the center C of the rearing tank 2. In addition, the water discharge pipe 51 may be arranged, for example, at substantially the same position as the water injection pipe 41. In the vertical direction, at least a part of the water injection pipe 41 and at least a part of the water discharge pipe 51 may be at the same height position. A distance between the water injection pipe 41 and the water discharge pipe 51 may be less than the maximum lateral width of the water discharge pipe 51 in plan view. The distance between the water injection pipe 41 and the water discharge pipe 51 may be less than the maximum lateral width of the water injection pipe 41 in plan view.

As illustrated in FIG. 1B, the openings 51a of the water discharge pipe 51 may be provided not in a direction facing the water injection pipe 41 but in a side surface on a side away from the water injection pipe 41. In this case, the water supplied through the openings 41a into the rearing tank 2 is prevented from being directly introduced into the water discharge pipe 51. In addition, as illustrated in FIG. 1B, when the openings 41a and the openings 51a face in opposite directions to each other, it is possible to make it difficult to deposit organic substances by applying a laterally rotating water flow.

The aeration equipment 6 is installed, for example, on the bottom of the water at the center C of the rearing tank 2, and is configured to supply air taken into the rearing tank 2 by an air pump or the like into the water W as bubbles. During rearing of the cephalopod larvae, an oxygen concentration of water may be measured, and the cephalopod rearing apparatus 1 may be configured to appropriately adjust the oxygen concentration by the aeration equipment 6 so that the oxygen concentration does not affect the rearing. The aeration equipment 6 may include a gas supply unit 61 configured to release bubbles into water, and a gas pipe 62 that is connected to an air pump (not illustrated) and configured to supply air taken in by the air pump to the gas supply unit 61. As illustrated in FIGS. 1A and 1B, when an aeration operation is performed in a state where the gas supply unit 61 is arranged at the bottom of water at the center C of the rearing tank 2, a flow of rising bubbles can be formed near the center C in the rearing tank 2.

A method of supplying air into the water W in the rearing tank 2 without using the aeration equipment 6 is, for example, a method of providing the water injection unit 4 above the water. The water injection unit 4 is arranged at a position away from the water surface and salt water for rearing is dropped from the water injection unit 4, thereby making it possible to mix air into the water with the dropping of the salt water. For example, the water injection pipe 41 of the water injection unit 4 is arranged at a position away from the water surface, and the water injection pipe 41 drops salt water into the water. As described above, the method of supplying air into the water W in the rearing tank 2 is not limited to the method using the aeration equipment 6.

In the cephalopod rearing apparatus 1 described above, water exchange in the rearing tank 2 can be performed by simultaneously performing water injection by the water injection unit 4 and water discharge by the water discharge unit 5. By making the amount of water injected per unit time by the water injection unit 4 equal to the amount of water discharged per unit time by the water discharge unit 5, water exchange is carried out while the amount of water in the rearing tank 2 is maintained. The amount of water in the rearing tank 2 may be secured to such an extent that the rearing of the cephalopod larvae is not hindered, and the amount of water injected and the amount of water discharged may not be the same. Although the exchange of water in the rearing tank 2 is necessary for the cephalopod larvae, either one or both water injection and water discharge may be temporarily stopped as long as the amount of water that does not hinder rearing is secured and water quality is not affected.

As described above, when the water injection unit 4 and the water discharge unit 5 perform the injection and discharge of water, while the aeration equipment 6 is operated, water exchange is performed in a state where a flow F in a circumferential direction from the water injection pipe 41 to the water discharge pipe 51 is formed as indicated by an arrow F illustrated in FIG. 1B, for example. The flow F in the circumferential direction can be formed according to the formation position of the openings 41a of the water injection pipe 41 and the formation position of the openings 51a of the water discharge pipe 51. When the aeration equipment 6 is operated, a part of the water flow is directed upward. As a result, a gentle circulating flow is formed also in the vertical direction.

As described above, the cephalopod rearing method using the cephalopod rearing apparatus 1 is a method of rearing cephalopod larvae in the rearing tank 2 including the water exchange unit 3 as the water exchange mechanism.

In the cephalopod rearing apparatus 1 and the cephalopod rearing method, the water exchange rate relative to the amount of water in the rearing tank 2 per day may be 200% or more, 210% or more, 220% or more, 230% or more, 240% or more, 250% or more, 260% or more, 270% or more, 280% or more, or 290% or more in the high water exchange rate period of the planktonic paralarval stage for the cephalopod larvae. An upper limit of the water exchange rate relative to the amount of water in the rearing tank 2 per day is not particularly limited as long as the cephalopod larvae can stably survive, and may be, for example, 2000% or less, 1800% or less, or 1500% or less. The high water exchange rate period may be set during the planktonic paralarval stage. A part of the planktonic paralarval stage may be the high water exchange rate period. The water exchange unit 3 of the cephalopod rearing apparatus 1 is configured to exchange water so that the water exchange rate is 200% or more in the high water exchange rate period. By setting the high water exchange rate period as described above and promoting water exchange in the rearing tank 2 during this period, the mortality rate of the cephalopod larvae in the rearing tank 2 can be suppressed.

During the cephalopod planktonic paralarval stage, the occurrence of protozoa in the water tank may cause the death of the cephalopod larvae. This is considered to be because protozoa enter the mantle and eat the cephalopod larvae. For this reason, the high water exchange rate period in which the water exchange rate is 200% or more is provided, whereby, even if protozoa occur in the water tank, it is possible to continue the rearing of the larvae while suppressing the proliferation of protozoa and to suppress the mortality rate of the cephalopod larvae.

Generally, during the rearing of cephalopod larvae, water exchange in the rearing tank 2 by the water exchange unit 3 is always performed. However, normally, the water exchange rate relative to the amount of water in the rearing tank 2 per day can be set to approximately from 10% to 100%. This water exchange rate is a value based on, for example, the following Literatures 1 to 3. When the amount of the water discharged from the rearing tank 2 is increased, the feed put into the rearing tank 2 also flows out. Therefore, in many cases, the water exchange rate is typically set to the above-described level to avoid the outflow of the feed. In this regard, when the high water exchange rate period is provided as described above, even if protozoa are generated in the rearing tank 2, their proliferation can be suppressed by using the water exchange. Therefore, the mortality rate of the cephalopod larvae in the rearing tank 2 can be suppressed.

Literature 1: Dan et al. (2018) An upwelling system for culturing common octopus paralarvae and its combined effect with supplying natural zooplankton on paralarval survival and growth.

Literature 2: Uriarte et al. (2010) Rearing and growth of the octopus *Robsonella fontaniana* (Cephalopoda: Octopodidae) From planktonic hatchings to benthic juveniles.

Literature 3: Villanueva et al. (2002) Growth and proteolytic activity of *Octopus vulgaris* paralarvae with different food rations during first feeding, using *Artemia nauplii* and compound diets.

The high water exchange rate period may be set to a rearing period until the cephalopod larvae reach 15 days after hatching. This is because, in the rearing period until the cephalopod larvae reach 15 days after hatching, the mortality rate which is expected to be caused by protozoa proliferation may be increased. Therefore, by setting the high water exchange rate period in the above-described period, the mortality rate can be effectively suppressed. In the rearing period until the cephalopod larvae reach 15 days after hatching, at least a part of the period may be the high water exchange rate period. The rearing period until the cephalopod larvae reach 15 days after hatching corresponds to a period from 0 days after hatching to 15 days after hatching. Note that the high water exchange rate period may be set in the rearing period until the cephalopod larvae reach 15 days after hatching, and the high water exchange rate period may also be set in the period after the cephalopod larvae reach 16 days after hatching. As described above, the high water exchange rate period can be set to include a period until the cephalopod larvae reach 15 days after hatching.

The high water exchange rate period may be set to a period after the cephalopod larvae reach 5 days after hatching. The larvae are particularly small during a period from hatching to 5 days after hatching of the larvae, and thus, if the high water exchange rate period is set, the larvae may possibly be discharged to the outside together with the water in the water tank during water discharge. Therefore, the high water exchange rate period may be set to a period after the cephalopod larvae reach 5 days after hatching. In addition, the occurrence of protozoa is easily confirmed from a time when approximately 3 to 5 days have passed since the hatching of the cephalopod larvae. Therefore, with the above setting, the mortality rate can be effectively suppressed. At least a part of the period after the cephalopod larvae reach 5 days after hatching may be the high water exchange rate period. When the high water exchange rate period is set in the period after the cephalopod larvae reach 5 days after hatching, in a rearing period until the cephalopod larvae reach 4 days after hatching, at least a part of the period may be the high water exchange rate period, or the high water exchange rate period may not be set. The rearing period until the cephalopod larvae reach 4 days after hatching corresponds to a period from 0 days after hatching to 4 days after hatching.

Before the high water exchange rate period, an adjustment period may be included in which the water exchange rate relative to the amount of water in the rearing tank 2 per day by the water exchange unit 3 is 80% or less, 90% or less, or 100% or less. A lower limit of the water exchange rate relative to the amount of water in the rearing tank 2 per day by the water exchange unit 3 is not particularly limited as long as the cephalopod larvae can stably survive, and may be, for example, 0% or more, 10% or more, or 20% or more. The adjustment period involves a lower water exchange rate and a lower water exchange speed in the rearing tank 2, than those in the high water exchange rate period. In this state, it is considered that the proliferation of protozoa is likely to occur as compared with that in the high water exchange rate period. On the other hand, the outflow of the feed in the water is suppressed, and thus the growth of the cephalopod larvae can be promoted. This adjustment period can also be a period in which the status of the cephalopod larvae in the rearing tank 2, for example, a change in the mortality rate, is checked. Further, the adjustment period may be set to a period until the cephalopod larvae reach 10 days after hatching. As described above, in a period in which the number of days after hatching of cephalopod larvae is small, if the water exchange rate is high, the cephalopod larvae cannot come into contact with the feed because the feed flows out and may possibly die due to starvation, or the cephalopod larvae cannot withstand the flow so that they cannot perform a swimming action for feed capturing and may possibly die due to starvation. For this reason, in the cephalopod rearing apparatus 1 and the cephalopod rearing method, the growth of the cephalopod larvae may be promoted while the outflow of the cephalopod larvae is suppressed by setting the adjustment period to a period until the cephalopod larvae reach 10 days after hatching. In the period until the cephalopod larvae reach 10 days after hatching, at least a part of the period may be the adjustment period. The period until the cephalopod larvae reach 10 days after hatching corresponds to a period from 0 days after hatching to 10 days after hatching. The water exchange unit 3 of the cephalopod rearing apparatus 1 may be configured to exchange water so that the water exchange rate is 100% or less in the adjustment period before the high water exchange rate period.

The rearing period from hatching of the cephalopod larvae to 15 days after hatching may include only the high water exchange rate period, and may include a combination of the adjustment period and the high water exchange rate period as described above. Furthermore, the adjustment period, the high water exchange rate period, and an intermediate period in which the water exchange rate is between that in the adjustment period and that in the high water exchange rate period may be combined. As an example, the periods may be set so that the adjustment period, the intermediate period, and the high water exchange rate period are sequentially set from the time of hatching in the rearing period from hatching to 15 days after hatching of the cephalopod larvae. In this case, as the days after hatching of the cephalopod larvae increase, the water exchange rate in the rearing tank 2 will be increased. Further, even in the middle of each of the periods, the high water exchange rate period may be set at any time according to the situation in the rearing tank 2.

The high water exchange rate period may be a continuous period of 1 minute or more, 5 minutes or more, 10 minutes or more, 30 minutes or more, 1 hour or more, 3 hours or more, 5 hours or more, 7 hours or more, 10 hours or more, or 12 hours or more. By providing the continuous high water exchange rate period in the above range, even if protozoa proliferate in the rearing tank 2, the proliferation of the protozoa by high-speed water exchange can be realized. Even if the high water exchange rate period is short, water exchange is promoted, and thus the proliferation of protozoa is suppressed and the mortality rate of cephalopod larvae can be suppressed. An upper limit of the above range has no problem as long as there is no influence on the rearing of cephalopod larvae. For example, the high water exchange rate period may be a continuous period of 19 days or less, 18 days or less, 15 days or less, 12 days or less, or 10 days or less.

In the cephalopod rearing apparatus 1, since the water discharge pipe 51 as the water discharge mechanism of the water discharge unit 5 of the water exchange unit 3 is provided in the vicinity of the bottom of the water in the rearing tank 2, water discharge is performed in the vicinity of the bottom of the water. It is known that protozoa are likely to proliferate in the vicinity of the bottom of the water in the rearing tank 2. This is because organic substances and the like in water, which are considered to be involved in the proliferation of protozoa, such as feeds floating in the water or dead larvae, precipitate and stay at the bottom of the water. For this reason, when the water discharge pipe 51 is provided in the vicinity of the bottom of water in the rearing tank 2 as described above, it is considered that organic substances and the like staying at the bottom of water at the time of water exchange can also be discharged out of the tank. Therefore, the mortality rate of cephalopod larvae can be suppressed.

It can also be said that the cephalopod rearing apparatus 1 and the cephalopod rearing method described above are an apparatus and a technique that are capable of controlling the density of protozoa present in the rearing tank 2 by the operation of the water exchange unit 3. That is, the cephalopod rearing apparatus 1 and the cephalopod rearing method may control the density of protozoa so that the density of protozoa of the water in the rearing tank 2 is 350 protozoa/ml or less, 400 protozoa/ml or less, 450 protozoa/ml or less, or 500 protozoa/ml or less in the planktonic paralarval stage. By providing the high water exchange rate period in which the water exchange rate per day is 200% or more as described above, it is possible to discharge the protozoa that may remain particularly at the bottom of the water to the outside of the system, thereby to adjust the density of protozoa in water to be low by water exchange. Therefore, the density of protozoa is controlled so that the density of protozoa is not more than the above-mentioned range, whereby the proliferation of protozoa can be suppressed, and the mortality rate of cephalopod larvae can be suppressed. Protozoa may be mixed into the cephalopod rearing apparatus 1 from rearing water or feeds, and the density of protozoa may be 0.01 individuals/ml or more, 0.1 individuals/ml or more, or 1 individual/ml or more.

When a common octopus is reared as the cephalopod, examples of protozoa that can be generated in the rearing tank 2 include flagellates and ciliates. More specific examples of the flagellates include *Ichthyobodo necator*, and examples of the ciliates include *Uronema marinum, Philasterides dicentrarchi, Pseudocohnilembus persalinus, Pseudorhabdosynochus hargisi*, and *Metanophrys sinensis*. Therefore, when rearing is performed using the cephalopod rearing apparatus 1 described above, the protozoa whose density is to be measured may be ciliates. In this case, the generation state of the protozoa in the rearing tank 2 can be grasped with higher accuracy.

Protozoa Prevention Method

The configuration according to the present embodiment can also be said to be a method of preventing the occurrence of protozoa, that is, a protozoa prevention method. That is, the method of preventing the occurrence of protozoa using the cephalopod rearing apparatus 1 is a method of preventing the occurrence of protozoa in the rearing tank 2 when rearing cephalopod larvae in the rearing tank 2 including the water exchange unit 3 as the water exchange mechanism. In this case, examples of the protozoa whose occurrence is to be prevented include flagellates and ciliates. More specific examples of the flagellates include *Ichthyobodo necator*, and examples of the ciliates include *Uronema marinum, Philasterides dicentrarchi, Pseudocohnilembus persalinus, Pseudorhabdosynochus hargisi*, and *Metanophrys sinensis*.

The method of preventing the occurrence of protozoa includes a high water exchange rate period in which a water exchange rate relative to an amount of water in the rearing tank 2 per day by the water exchange unit 3 as the water exchange mechanism is 200% or more in a planktonic paralarval stage of cephalopod larvae. By setting the high water exchange rate period as described above and promoting water exchange in the rearing tank 2 during the period, the occurrence of protozoa in the rearing tank 2 can be prevented, and the mortality rate of the cephalopod larvae can be suppressed.

The high water exchange rate period may be set to a rearing period until the cephalopod larvae reach 15 days after hatching. This is because, in the rearing period until the cephalopod larvae reach 15 days after hatching, the mortality rate which is expected to be caused by the occurrence and proliferation of protozoa may be increased. Therefore, by setting the high water exchange rate period in the above-described period, the mortality rate can be effectively suppressed. In the rearing period until the cephalopod larvae reach 15 days after hatching, at least a part of the period may be the high water exchange rate period. Note that the high water exchange rate period may be set in the rearing period until the cephalopod larvae reach 15 days after hatching, and the high water exchange rate period may also be set in the period after the cephalopod larvae reach 16 days after hatching. As described above, the high water exchange rate period can be set to include a period until the cephalopod larvae reach 15 days after hatching.

The high water exchange rate period may be set to a period after the cephalopod larvae reach 5 days after hatching. The occurrence of protozoa is easily confirmed from a time when approximately 3 to 5 days have passed since the hatching of the cephalopod larvae. Therefore, with the above setting, the mortality rate can be effectively suppressed. At least a part of the period after the cephalopod larvae reach 5 days after hatching may be the high water exchange rate period. When the high water exchange rate period is set in the period after the cephalopod larvae reach 5 days after hatching, in a rearing period until the cephalopod larvae reach 4 days after hatching, at least a part of the period may be the high water exchange rate period, or the high water exchange rate period may not be set.

Before the high water exchange rate period, an adjustment period may be included in which the water exchange rate relative to the amount of water in the rearing tank 2 per day by the water exchange unit 3 is 80% or less, 90% or less, or 100% or less. A lower limit of the water exchange rate relative to the amount of water in the rearing tank 2 per day by the water exchange unit 3 is not particularly limited as long as the cephalopod larvae can stably survive, and may be, for example, 0% or more, 10% or more, or 20% or more. The adjustment period involves a lower water exchange rate and a lower water exchange speed in the rearing tank 2, than those in the high water exchange rate period. In this state, it is considered that protozoa are likely to be generated as compared with that in the high water exchange rate period. On the other hand, the outflow of the feed in the water is suppressed, and thus the growth of the cephalopod larvae can be promoted. This adjustment period can also be a period in which the status of the cephalopod larvae in the rearing tank 2, for example, a change in the mortality rate, is checked. Further, the adjustment period may be set to a period until the cephalopod larvae reach 10 days after hatching. As described above, in a period in which the number of days after hatching of cephalopod larvae is small, the cephalopod larvae may flow out when the water exchange rate is high. For this reason, in the protozoa prevention method, the growth of the cephalopod larvae may be promoted while the outflow of the cephalopod larvae is suppressed by setting the adjustment period to a period until the cephalopod larvae reach 10 days after hatching. In the period until the cephalopod larvae reach 10 days after hatching, at least a part of the period may be the adjustment period.

The rearing period from hatching of the cephalopod larvae to 15 days after hatching include only the high water exchange rate period, but may include a combination of the adjustment period and the high water exchange rate period as described above. Furthermore, the adjustment period, the high water exchange rate period, and an intermediate period in which the water exchange rate is between that in the adjustment period and that in the high water exchange rate period may be combined. As an example, the periods may be set so that the adjustment period, the intermediate period, and the high water exchange rate period are sequentially set from the time of hatching, for the rearing period from hatching to 15 days after hatching of the cephalopod larvae. In this case, as the days after hatching of the cephalopod larvae increases, the water exchange rate in the rearing tank 2 will be increased. Further, even in the middle of each of the periods, the high water exchange rate period may be set at any time according to the situation in the rearing tank 2.

The high water exchange rate period may be a continuous period of 1 minute or more, 5 minutes or more, 10 minutes or more, 30 minutes or more, 1 hour or more, 3 hours or more, 5 hours or more, 7 hours or more, 10 hours or more, or 12 hours or more. By providing the continuous high water exchange rate period in the above range, even if protozoa occur in the rearing tank 2, the proliferation of the protozoa by high-speed water exchange can be realized. Even if the high water exchange rate period is short, water exchange is promoted, and thus the proliferation of protozoa is suppressed and the mortality rate of cephalopod larvae can be suppressed. An upper limit of the above range is not problematic as long as there is no influence on the rearing of cephalopod larvae. For example, the high water exchange rate period may be a continuous period of 19 days or less, 18 days or less, 15 days or less, 12 days or less, or 10 days or less.

In the cephalopod rearing apparatus 1, since the water discharge pipe 51 as the water discharge mechanism of the water discharge unit 5 of the water exchange unit 3 is provided in the vicinity of the bottom of the water in the rearing tank 2, water discharge is performed in the vicinity of the bottom of the water. It is presumed that, in the rearing tank 2, protozoa are likely to be generated in the vicinity of the bottom of the water. This is because organic substances and the like in the water, which are considered to be involved in the proliferation of protozoa, such as feeds floating in the water or dead larval bodies, precipitate and stay at the bottom of the water. For this reason, when the water discharge pipe 51 is provided in the vicinity of the bottom of the water in the rearing tank 2 as described above, organic substances and the like staying at the bottom of the water at the time of water exchange can also be discharged out of the water tank. Therefore, it is considered that the occurrence and proliferation of protozoa are suppressed, and the mortality rate of cephalopod larvae can be suppressed.

It can also be said that the protozoa prevention method by the cephalopod rearing apparatus 1 is a technique for controlling the density of protozoa present in the rearing tank 2 by the operation of the water exchange unit 3. That is, the protozoa prevention method may control the density of protozoa so that the density of protozoa in the water in the rearing tank 2 is 350 protozoa/ml or less, 400 protozoa/ml or less, 450 protozoa/ml or less, or 500 protozoa/ml or less in the planktonic paralarval stage. By providing the high water exchange rate period in which the water exchange rate per day is 200% or more as described above, it is possible to discharge the protozoa generated particularly at the bottom of the water to the outside of the system, thereby to adjust the density of protozoa in the water to be low by water exchange even if protozoa are generated. Therefore, the density of protozoa is controlled so that the density of protozoa is not more than the above-mentioned range, whereby the occurrence of protozoa can be suppressed, and the mortality rate of cephalopod larvae can be suppressed. Protozoa may be mixed into the cephalopod rearing apparatus 1 from rearing water or feeds, and the density of protozoa may be controlled to achieve 0.01 individuals/ml or more, 0.1 individuals/ml or more, or 1 individual/ml or more.

Protozoa Extermination Method

The configuration according to the present embodiment can also be said to be a method of exterminating protozoa in the rearing tank 2, that is, a protozoa extermination method. That is, the method of exterminating protozoa using the cephalopod rearing apparatus 1 is a method of exterminating protozoa from the inside of the rearing tank 2 when rearing cephalopod larvae in the rearing tank 2 including the water exchange unit 3 as the water exchange mechanism. In this case, examples of the protozoa to be exterminated include flagellates and ciliates. More specific examples of the flagellates include *Ichthyobodo necator*, and examples of the ciliates include *Uronema marinum, Philasterides dicentrarchi, Pseudocohnilembus persalinus, Pseudorhabdosynochus hargisi*, and *Metanophrys sinensis*.

The method of exterminating protozoa includes a high water exchange rate period in which a water exchange rate relative to an amount of water in the rearing tank 2 per day by the water exchange unit 3 as the water exchange mechanism is 200% or more in a planktonic paralarval stage of cephalopod larvae. By setting the high water exchange rate period as described above and promoting water exchange in the rearing tank 2 during the period, the protozoa in the rearing tank 2 can be exterminated, and the mortality rate of the cephalopod larvae can be suppressed.

The high water exchange rate period may be set to a rearing period until the cephalopod larvae reach 15 days after hatching. This is because, in the rearing period until the cephalopod larvae reach 15 days after hatching, the mortality rate which is expected to be caused by the occurrence and proliferation of protozoa may be increased. Therefore, by setting the high water exchange rate period in the above-described period, the mortality rate can be effectively suppressed. In the rearing period until the cephalopod larvae reach 15 days after hatching, at least a part of the period may be the high water exchange rate period. Note that the high water exchange rate period may be set in the rearing period until the cephalopod larvae reach 15 days after hatching, and the high water exchange rate period may also be set in the period after the cephalopod larvae reach 16 days after hatching. As described above, the high water exchange rate period can be set to include a period until the cephalopod larvae reach 15 days after hatching.

The high water exchange rate period may be set to a period after the cephalopod larvae reach 5 days after hatching. In the rearing tank 2, protozoa are likely to be confirmed to be generated from a time when approximately 3 to 5 days have passed since the hatching of the cephalopod larvae. Therefore, with the above setting, protozoa can be appropriately removed and the mortality rate can be effectively suppressed. At least a part of the period after the cephalopod larvae reach 5 days after hatching may be the high water exchange rate period. When a high water exchange period is set after the 5 days after hatching for cephalopod larvae, the rearing period up to 4 days of age (from day 0 to day 4) may include at least part of the time as a high water exchange period, or it may not include a high water exchange period at all.

Before the high water exchange rate period, an adjustment period may be included in which the water exchange rate relative to the amount of water in the rearing tank 2 per day by the water exchange unit 3 is 80% or less, 90% or less, or 100% or less. A lower limit of the water exchange rate relative to the amount of water in the rearing tank 2 per day by the water exchange unit 3 is not particularly limited as long as the cephalopod larvae can stably survive, and may be, for example, 0% or more, 10% or more, or 20% or more. The adjustment period involves a lower water exchange rate and a lower water exchange speed in the rearing tank 2, than those in the high water exchange rate period. In this state, it is considered that protozoa are likely to be generated as compared with that in the high water exchange rate period.

On the other hand, the outflow of the feed in the water is suppressed, and thus the growth of the cephalopod larvae can be promoted. This adjustment period can also be a period in which the status of the cephalopod larvae in the rearing tank 2, for example, a change in the mortality rate, is checked. Further, the adjustment period may be set to a period until the cephalopod larvae reach 10 days after hatching. As described above, in a period in which the number of days after hatching of cephalopod larvae is small, the cephalopod larvae may flow out when the water exchange rate is high. For this reason, in the protozoa extermination method, the growth of the cephalopod larvae may be promoted while the outflow of the cephalopod larvae is suppressed by setting the adjustment period to a period until the cephalopod larvae reach 10 days after hatching. In the period until the cephalopod larvae reach 10 days after hatching, at least a part of the period may be the adjustment period.

The rearing period from hatching of the cephalopod larvae to 15 days after hatching may include only the high water exchange rate period, but may include a combination of the adjustment period and the high water exchange rate period as described above. Furthermore, the adjustment period, the high water exchange rate period, and an intermediate period in which the water exchange rate is between that in the adjustment period and that in the high water exchange rate period may be combined. As an example, the periods may be set so that the adjustment period, the intermediate period, and the high water exchange rate period are sequentially set from the time of hatching, for the rearing period from hatching to 15 days after hatching of the cephalopod larvae. In this case, as the days after hatching of the cephalopod larvae increases, the water exchange rate in the rearing tank 2 will be increased. Further, even in the middle of each of the periods, the high water exchange rate period may be set at any time according to the situation in the rearing tank 2.

The high water exchange rate period may be a continuous period of 1 minute or more, 5 minutes or more, 10 minutes or more, 30 minutes or more, 1 hour or more, 3 hours or more, 5 hours or more, 7 hours or more, 10 hours or more, or 12 hours or more. By providing the continuous high water exchange rate period in the above range, even if protozoa are generated in the rearing tank 2, the protozoa can be appropriately exterminated by high-speed water exchange. Even if the high water exchange rate period is short, water exchange is promoted, and thus the protozoa are exterminated and the mortality rate of cephalopod larvae can be suppressed. An upper limit of the above range poses no problem as long as there is no influence on the rearing of cephalopod larvae. For example, the high water exchange rate period may be a continuous period of 19 days or less, 18 days or less, 15 days or less, 12 days or less, or 10 days or less.

In the cephalopod rearing apparatus 1, since the water discharge pipe 51 as the water discharge mechanism of the water discharge unit 5 of the water exchange unit 3 is provided in the vicinity of the bottom of the water in the rearing tank 2, water discharge is performed in the vicinity of the bottom of the water. It is presumed that, in the rearing tank 2, the protozoa are likely to be generated in the vicinity of the bottom of the water. This is because organic substances and the like in the water, which are considered to be involved in the proliferation of the protozoa, such as feeds floating in the water and dead larval bodies, precipitate and stay at the bottom of the water. For this reason, when the water discharge pipe 51 is provided in the vicinity of the bottom of the water in the rearing tank 2 as described above, organic substances and the like stay at the bottom of the water at the time of water exchange, in addition to the protozoa staying at the bottom of the water, can also be discharged to the outside of the water tank. Therefore, it is considered that the extermination of the protozoa is promoted and the occurrence and proliferation of the protozoa are suppressed, and the mortality rate of cephalopod larvae can be suppressed.

It can also be said that the protozoa extermination method by the cephalopod rearing apparatus 1 is a technique for controlling the density of the protozoa present in the rearing tank 2 by the operation of the water exchange unit 3. That is, the protozoa extermination method may control the density of protozoa so that the density of protozoa in the water in the rearing tank 2 is 350 protozoa/ml or less, 400 protozoa/ml or less, 450 protozoa/ml or less, or 500 protozoa/ml or less in the planktonic paralarval stage. By providing the high water exchange rate period in which the water exchange rate per day is 200% or more as described above, it is possible to exterminate the protozoa present particularly at the bottom of water by discharging them to the outside of the system, thereby to adjust the density of protozoa in the water to be low by water exchange even if protozoa are generated. Therefore, the density of protozoa is controlled so that the density of protozoa is not more than the above-mentioned range, whereby the protozoa in the rearing tank 2 can be appropriately exterminated, and the mortality rate of cephalopod larvae can be suppressed.

Evaluation Example

1. Evaluation of Density of Protozoa and Daily Mortality Rate Resulting from the Setting of a High Water Exchange Rate Period Using the cephalopod rearing apparatus 1 illustrated in FIGS. 1A and 1B, larvae of common octopus as a type of cephalopod were reared from 0 days after hatching to 18 days after hatching. More specifically, 3000 common octopus larvae of 0 days after hatching were put into the rearing tank 2 having a volume of 500 L, and then reared until 18 days after hatching. The water exchange rate in the rearing tank 2 was set at three levels shown in Table 1 below in accordance with the days after hatching of the common octopus larvae, and the water exchange unit 3 was controlled to achieve the water exchange rate. In this state, the protozoa densities and daily mortality rates at 0, 3, 6, 9, 12, 15, and 18 days after hatching were measured. The results are shown in Table 2.

TABLE 1

| Period | Days after hatching | Water exchange rate |
|---|---|---|
| T1 | 0 to 6 | 77%/day |
| T2 | 7 to 15 | 288%/day |
| T3 | 16 to 18 | 480 to 960%/day |

TABLE 2

| Days after hatching | Density of protozoa (individuals/ml) | Daily mortality rate (%) |
|---|---|---|
| 0 | 0 | 0.00 |
| 3 | 45 | 0.91 |
| 6 | 350 | 1.48 |
| 9 | 315 | 10.26 |

TABLE 2-continued

| Days after hatching | Density of protozoa (individuals/ml) | Daily mortality rate (%) |
|---|---|---|
| 12 | 315 | 8.39 |
| 15 | 150 | 8.09 |
| 18 | 15 | 0.51 |

A period T1 corresponds to the adjustment period, and each of periods T2 and T3 corresponds to the high water exchange rate period. In period T3, the water exchange rate was changed depending on the time zone, and the operation was performed under the condition of 480% or more per day.

As for the density of protozoa in the rearing tank 2, 50 ml of rearing water near the bottom surface of the rearing tank 2 was collected, 20 μl of the collected rearing water was subjected to visual measurement under microscopic observation, and the density of protozoa per mL was calculated. In addition, the daily mortality rate of the common octopus larvae was calculated by counting the number of dead larvae in water discharged during cleaning.

According to the results shown in Table 2, it was confirmed that, in the rearing tank 2, the protozoa increased after the common octopus larvae reached 3 days after hatching. After entering into the period T2 in which the water exchange rate was 200% or more, the density of protozoa decreased, and the daily mortality rate also decreased.

In addition, from the results shown in Table 2, it was confirmed that the daily mortality rate varied similarly to the density of protozoa. However, the change in the daily mortality rate is slightly delayed from the change in the density of protozoa. For example, even after the high water exchange rate period of the period T2 is started, the daily mortality rate increased. However, it was confirmed that the daily mortality rate gradually decreased after several days. From this result, it was confirmed that the density of protozoa in the rearing tank 2 can be controlled to a certain value or less and the mortality rate of the cephalopod larvae can be suppressed, by providing the high water exchange rate period. The next day after the end of the 18-day test, no protozoa were observed and the mortality rate was also 0. Further, the generated protozoa, when examined by 18S rRNA gene sequence analysis, were confirmed to be *Metanophrys sinensis*.

2. Evaluation of Arrangement of the Water Injection Unit, the Water Discharge Unit, and Common Octopus Survival Rate Next, using the cephalopod rearing apparatus 1 illustrated in FIGS. 1A and 1B, larvae of the common octopus as a type of cephalopod were reared from 0 days after hatching to 18 days after hatching, and the survival rate of common octopus larvae was evaluated.

On the other hand, as a configuration of a comparative example, using an apparatus in which the water injection pipe 41 of the water injection unit 4 was provided in the vicinity of the water surface of the rearing tank 2 and the water discharge pipe 51 of the water discharge unit 5 was provided to extend in the vertical direction at the center of the rearing tank 2, common octopus larvae were reared from 0 days after hatching to 18 days after hatching, and the survival rate of common octopus larvae was evaluated. In the configuration of the comparative example, the water injection pipe 41 is configured to inject water into the rearing tank 2 from the vicinity of the water surface of the rearing tank 2 in the circumferential direction of the rearing tank 2. On the other hand, a circulating flow in the circumferential direction and the vertical direction in the rearing tank 2 is formed by discharging water through the water discharge pipe 51 provided at the center.

To each of the rearing tanks 2, 3000 common octopus larvae of 0 days after hatching were charged and then reared until 18 days after hatching. The water exchange rate in the rearing tank 2 according to the days after hatching of the common octopus larvae was set to be the same as that under the conditions shown in Table 1. In this state, the survival rates of the common octopus at 0, 3, 6, 9, 12, 15, and 18 days after hatching were calculated as proportions of the number of remaining larvae relative to the number of larvae at 0 days after hatching of 100%. The results are shown in Table 3. Table 3 shows the results of the survival rates of the common octopus measured until 18 days after hatching.

TABLE 3

| Days after hatching | Survival rate (%) in injection/discharge of water in the vicinity of the water surface | Survival rate (%) in injection/discharge of water at the bottom surface |
| --- | --- | --- |
| 0 | 100 | 100 |
| 3 | 99 | 99 |
| 6 | 98 | 95 |
| 9 | 90 | 90 |
| 12 | 44 | 71 |
| 15 | 29 | 55 |
| 18 | 20 | 50 |

According to the results shown in Table 3, it was confirmed that in the rearing tank 2, the survival rates under the respective conditions became different, after the common octopus larvae reached 9 days after hatching. It was confirmed that when using the apparatus from the comparative example where the placement of the water injection pipe 41 and the discharge pipe 51 differs, the survival rate was less than 50% at 12 days after hatching. On the other hand, when the cephalopod was reared in apparatus 1 illustrated in FIGS. 1A and 1B, the survival rate was 50% or more at 15 days after hatching, and it was confirmed that the survival rate was higher than that when the apparatus of the comparative example was used, even at 18 days after hatching.

Modified Examples

Although embodiments of the present disclosure have been described above, the cephalopod rearing method, the cephalopod rearing apparatus, the protozoa prevention method, and the protozoa extermination method according to the present disclosure are not limited to those of the above-described embodiments.

For example, although the case where the cephalopod is a common octopus has been described in the above-described embodiment, the rearing conditions may be appropriately changed as necessary, in a case where larvae of other cephalopods are reared. In one example among various examples described in the present disclosure, at least some of the matters described in the other examples may be applied.

REFERENCE SIGNS LIST

1. Cephalopod rearing apparatus, 2. Rearing tank, 3. Water exchange unit, 4. Water injection unit, 5. Water discharge unit, 6. Aeration equipment, 21. Bottom wall, 41.

Water injection pipe, 41*a*. Opening, 42. Pipe, 51. Water discharge pipe, 51*a*. Opening, 52. Pipe, 61. Gas supply unit, 62. Gas pipe.

The invention claimed is:

1. A cephalopod rearing method comprising rearing cephalopod larvae in a rearing tank comprising a water exchange mechanism, wherein the cephalopod larvae are common octopus larvae, and wherein a planktonic paralarval stage for the cephalopod larvae includes (i) a high water exchange rate period in which a water exchange rate relative to an amount of water in the rearing tank per day by a water exchange mechanism is 200% or more, and (ii) an adjustment period before the high water exchange rate period, in which the water exchange rate relative to the amount of water in the rearing tank per day by the water exchange mechanism is 90% or less.

2. The cephalopod rearing method according to claim 1, wherein the high water exchange rate period is set to include a period until the cephalopod larvae reach 15 days after hatching.

3. The cephalopod rearing method according to claim 1, wherein the high water exchange rate period is a continuous period of 12 hours or more.

4. The cephalopod rearing method according to claim 1, wherein the high water exchange rate period is set to a period after the cephalopod larvae reach 5 days after hatching.

5. The cephalopod rearing method according to claim 1, wherein the adjustment period is set to a period until the cephalopod larvae reach 10 days after hatching.

6. The cephalopod rearing method according to claim 1, wherein the water exchange mechanism is configured to discharge water in the vicinity of a bottom of water in the rearing tank.

7. The cephalopod rearing method according to claim 1, wherein the water exchange rate relative to the amount of water in the rearing tank per day by the water exchange mechanism during the adjustment period is 80% or less.

8. A method of preventing protozoa occurrence in a rearing tank with cephalopod larvae, comprising rearing cephalopod larvae in the rearing tank having a water exchange mechanism, wherein the cephalopod larvae are common octopus larvae, and wherein a planktonic paralarval stage for the cephalopod larvae includes (i) a high water exchange rate period in which a water exchange rate relative to an amount of water in the rearing tank per day by the water exchange mechanism is 200% or more, and (ii) an adjustment period before the high water exchange rate period, in which the water exchange rate relative to the amount of water in the rearing tank per day by the water exchange mechanism is 90% or less, thereby preventing protozoa occurrence in the rearing tank.

9. The protozoa prevention method according to claim 8, wherein the high water exchange rate period is set to include a period until the cephalopod larvae reach 15 days after hatching.

10. The protozoa prevention method according to claim 8, wherein the high water exchange rate period is a continuous period of 12 hours or more.

11. The protozoa prevention method according to claim 8, wherein the high water exchange rate period is set to a period after the cephalopod larvae reach 5 days after hatching.

12. The protozoa prevention method according to claim 8, wherein the adjustment period is set to a period until the cephalopod larvae reach 10 days after hatching.

13. The protozoa prevention method according to claim 8, wherein the water exchange mechanism is configured to discharge water in the vicinity of a bottom of water in the rearing tank.

14. The protozoa prevention method according to claim 8, wherein the protozoa is a ciliate.

15. The protozoa prevention method according to claim 8, wherein, in the planktonic paralarval stage, a density of protozoa of water in the rearing tank is controlled to 400 individuals/ml or less.

16. The protozoa prevention method according to claim 8, wherein the water exchange rate relative to the amount of water in the rearing tank per day by the water exchange mechanism during the adjustment period is 80% or less.

17. A method of exterminating a protozoa in a rearing tank with cephalopod larvae, comprising rearing cephalopod larvae in the rearing tank having a water exchange mechanism, wherein the cephalopod larvae are common octopus larvae, and wherein a planktonic paralarval stage for the cephalopod larvae includes (i) a high water exchange rate period in which a water exchange rate relative to an amount of water in the rearing tank per day by the water exchange mechanism is 200% or more, and (ii) an adjustment period before the high water exchange rate period, in which the water exchange rate relative to the amount of water in the rearing tank per day by the water exchange mechanism is 90% or less, thereby exterminating the protozoa in the rearing tank.

18. The method according to claim 17, wherein the high water exchange rate period is set to include a period until the cephalopod larvae reach 15 days after hatching.

19. The method according to claim 17, wherein the high water exchange rate period is a continuous period of 12 hours or more.

20. The method according to claim 17, wherein the high water exchange rate period is set to a period after the cephalopod larvae reach 5 days after hatching.

21. The method according to claim 17, wherein the adjustment period is set to a period until the cephalopod larvae reach 10 days after hatching.

22. The method according to claim 17, wherein the water exchange mechanism is configured to discharge water in the vicinity of a bottom of water in the rearing tank.

23. The method according to claim 17, wherein the protozoa is a ciliate.

24. The method according to claim 17, wherein, in the planktonic paralarval stage, a density of protozoa of water in the rearing tank is controlled to 400 individuals/ml or less.

25. The method according to claim 17, wherein the water exchange rate relative to the amount of water in the rearing tank per day by the water exchange mechanism during the adjustment period is 80% or less.

* * * * *